(12) United States Patent
Sugimoto et al.

(10) Patent No.: US 8,902,494 B2
(45) Date of Patent: Dec. 2, 2014

(54) AMPLIFICATION OPTICAL FIBER WITH OPTICAL COMPONENT AND FIBER LASER DEVICE INCLUDING THE SAME

(75) Inventors: Ryo Sugimoto, Sakura (JP); Kuniharu Himeno, Sakura (JP)

(73) Assignee: Fujikura Ltd., Tokyo (JP)

( * ) Notice: Subject to any disclaimer, the term of this patent is extended or adjusted under 35 U.S.C. 154(b) by 706 days.

(21) Appl. No.: 13/072,918

(22) Filed: Mar. 28, 2011

(65) Prior Publication Data

US 2011/0235165 A1     Sep. 29, 2011

(30) Foreign Application Priority Data

Mar. 29, 2010 (JP) ................................. 2010-073990

(51) Int. Cl.
| | |
|---|---|
| *H01S 3/094* | (2006.01) |
| *G02B 6/24* | (2006.01) |
| *G02B 6/26* | (2006.01) |
| *G02B 6/02* | (2006.01) |
| *A61N 5/06* | (2006.01) |
| *H01S 3/067* | (2006.01) |

(52) U.S. Cl.
CPC ..... *H01S 3/094015* (2013.01); *A61N 2005/063* (2013.01); *H01S 3/094007* (2013.01); *G02B 6/262* (2013.01); *G02B 6/02042* (2013.01); *H01S 3/06754* (2013.01); *G02B 6/241* (2013.01)
USPC ........................... 359/341.32; 385/32; 385/50

(58) Field of Classification Search
CPC .......... H01S 3/06737; H01S 3/094003; H01S 3/094007; H01S 3/094011; H01S 3/094019; H01S 3/094023; H01S 3/094015; G02B 6/241; G02B 6/262

USPC .................................. 385/32, 50; 359/341.32
See application file for complete search history.

(56) References Cited

U.S. PATENT DOCUMENTS

| | | | | |
|---|---|---|---|---|
| 4,136,929 A | * | 1/1979 | Suzaki ............................. | 385/30 |
| 4,712,075 A | * | 12/1987 | Snitzer ........................ | 359/341.1 |
| 4,964,131 A | * | 10/1990 | Liu et al. ........................... | 372/6 |
| 5,048,026 A | * | 9/1991 | Shaw et al. ........................ | 372/6 |
| 5,136,420 A | * | 8/1992 | Inagaki et al. ............. | 359/341.3 |
| 5,339,372 A | * | 8/1994 | Miller et al. ................... | 385/29 |
| 5,867,305 A | * | 2/1999 | Waarts et al. ............ | 359/337.12 |
| 6,151,338 A | * | 11/2000 | Grubb et al. ...................... | 372/6 |

(Continued)

FOREIGN PATENT DOCUMENTS

| | | |
|---|---|---|
| JP | 11-052162 A | 2/1999 |
| JP | 2008-010804 A | 1/2008 |

(Continued)

*Primary Examiner* — Ari M Diacou
(74) *Attorney, Agent, or Firm* — Westerman, Hattori, Daniels & Adrian, LLP

(57) ABSTRACT

An amplification optical fiber with an optical component capable of efficiently absorbing pumping light and a fiber laser device including the same are provided.

An amplification optical fiber with an optical component in a fiber laser device 1 includes: an amplification optical fiber 30 having a core 31 doped with an active element and a clad 32 through which pumping light for amplifying light to be amplified propagating through the core 31 propagates; and an optical component 50 including at least one optical fiber 53a to 53f having a first end coupled to a portion of the clad 32 and a second end coupled to at least another portion of the clad 32 at one end 35 of the amplification optical fiber 30.

15 Claims, 5 Drawing Sheets

(56) References Cited

U.S. PATENT DOCUMENTS

| | | | |
|---|---|---|---|
| 6,434,295 B1* | 8/2002 | MacCormack et al. | 385/27 |
| 6,600,592 B2* | 7/2003 | Islam | 359/334 |
| 6,795,460 B1* | 9/2004 | Itoh | 372/34 |
| 7,016,573 B2* | 3/2006 | Dong et al. | 385/46 |
| 7,221,822 B2* | 5/2007 | Grudinin et al. | 385/30 |
| 7,492,993 B2* | 2/2009 | Nakai et al. | 385/46 |
| 7,526,165 B2* | 4/2009 | Nielsen et al. | 385/125 |
| 7,778,290 B2* | 8/2010 | Sacks et al. | 372/21 |
| 8,213,077 B2* | 7/2012 | Dong et al. | 359/341.1 |
| 2002/0044344 A1* | 4/2002 | Terahara | 359/341.1 |
| 2004/0196537 A1* | 10/2004 | Starodoumov | 359/341.3 |
| 2007/0280597 A1* | 12/2007 | Nakai et al. | 385/43 |
| 2009/0154882 A1* | 6/2009 | Salokatve | 385/50 |
| 2010/0142894 A1* | 6/2010 | Gonthier | 385/50 |
| 2010/0195678 A1* | 8/2010 | Kuka | 372/6 |
| 2012/0051692 A1* | 3/2012 | Seo et al. | 385/28 |
| 2012/0230352 A1* | 9/2012 | Minelly et al. | 372/6 |

FOREIGN PATENT DOCUMENTS

| | | |
|---|---|---|
| JP | 2009-212441 A | 9/2009 |
| JP | 2009-542028 A | 11/2009 |
| JP | 2010-028053 A | 2/2010 |
| WO | 2007/148139 A1 | 12/2007 |

\* cited by examiner

AMPLIFICATION OPTICAL FIBER WITH OPTICAL COMPONENT AND FIBER LASER DEVICE INCLUDING THE SAME

TECHNICAL FIELD

The invention relates to an amplification optical fiber with an optical component and a fiber laser device including the same, and more particularly to an amplification optical fiber with an optical component capable of efficiently absorbing pumping light and a fiber laser device including the same.

BACKGROUND ART

Fiber laser devices can produce a small beam spot of light having high focusing performance and high power density, and process in a noncontact manner. Accordingly, fiber laser devices are used in various fields such as the laser processing field and the medical field. In particular, fiber laser devices used in the processing field and the medical field are high power fiber laser devices.

A fiber laser device includes an amplification optical fiber having a core coated with a clad and doped with an active element for amplifying light. Pumping light propagating through the clad of the amplification optical fiber is absorbed by the active element, whereby the active element is pumped. Light to be amplified propagating through the core is amplified by stimulated emission of the active element and output therefrom. It is therefore desirable that pumping light input to the amplification optical fiber be efficiently absorbed by the active element without any loss. However, it is known that skew mode propagation may occur in the amplification optical fiber, where part of pumping light propagates only through the clad and is not absorbed by the active element.

Patent Document 1 listed below discloses an amplification optical fiber in which such skew mode propagation is suppressed. In the amplification optical fiber, the cross-sectional shape of a clad is square and scattering means for scattering pumping light is provided at a portion of the clad. The amplification optical fiber thus scatters skew mode light so that the scattered light passes through a core.
[Patent Document 1] Japanese Patent No. 3479219

SUMMARY OF THE INVENTION

However, it is difficult to scatter skew mode light completely, and light in skew mode that has not been scattered is output from the amplification optical fiber. Moreover, part of pumping light may be output from the amplification optical fiber without being absorbed by the active element even if it is not skew mode light. When part of pumping light is output in this manner, the amplification efficiency in the amplification optical fiber is low. There has therefore been a demand for higher efficiency in absorption of pumping light in the amplification optical fiber.

It is therefore an object of the invention to provide an amplification optical fiber with an optical component capable of efficiently absorbing pumping light and a fiber laser device including the same.

An amplification optical fiber with an optical component according to the invention includes: an amplification optical fiber having a core doped with an active element and a clad through which pumping light for amplifying light to be amplified propagating through the core propagates; and an optical component including at least one optical fiber having a first end coupled to a portion of the clad and a second end coupled to another portion of the clad at a first end of the amplification optical fiber.

According to such an amplification optical fiber with an optical component, even if pumping light is input to a second end of the amplification optical fiber or to a middle portion of the amplification optical fiber and output from the clad at the first end of the amplification optical fiber, pumping light output from a portion of the clad is input to the optical fiber of the optical component through the first end of the optical fiber. The pumping light then propagates through the optical fiber, is output through the second end of the optical fiber, and is input again to the amplification optical fiber. On the other hand, at least part of the pumping light output from another portion of the clad of the amplification optical fiber is input to the optical fiber of the optical component through the second end of the optical fiber. The pumping light then propagates through the optical fiber, is output through the first end of the optical fiber, and is input again to the clad of the amplification optical fiber. The pumping light thus input again to the amplification optical fiber is absorbed by the active element while passing through the core. As described above, according to the amplification optical fiber with an optical component, pumping light can be efficiently absorbed in the amplification optical fiber since pumping light output from the amplification optical fiber can be input again to the amplification optical fiber.

The term "couple" used herein means "optically couple" unless otherwise particularly mentioned.

Preferably, in the amplification optical fiber with an optical component described above, the portion of the clad to which the first end of the optical fiber is coupled is nearer to an outer periphery of the amplification optical fiber than the another portion of the clad to which the second end of the optical fiber is coupled.

According to such an amplification optical fiber with an optical component, pumping light output from the outer periphery of the clad can be input to the inner periphery of the clad at the first end of the amplification optical fiber. It is to be noted here that skew mode light of pumping light propagating through the clad of the amplification optical fiber propagates mainly through the outer periphery of the clad. According to such an optical component, skew mode light can therefore more easily propagate through the core in the amplification optical fiber by inputting the skew mode light output from the outer periphery of the clad to the inner periphery of the clad. Therefore, pumping light can be more efficiently absorbed in the amplification optical fiber.

More preferably, in the amplification optical fiber with an optical component described above, a cross-sectional area of the optical fiber at the first end is larger than that at the second end.

According to such an amplification optical fiber with an optical component, larger part of pumping light output from the outer periphery of the clad of the amplification optical fiber can be input to the inner periphery of the amplification optical fiber. Thus, larger part of the skew mode light can be input to the inner periphery of the clad of the amplification optical fiber via the optical fiber of the optical component.

Preferably, in the amplification optical fiber with an optical component described above, the optical fiber is jointless.

According to such an amplification optical fiber with an optical component, since there is no loss of pumping light caused by joint portions, pumping light output from the amplification optical fiber can be efficiently input again to the amplification optical fiber.

Preferably, in the amplification optical fiber with an optical component described above, the optical component includes a plurality of optical fibers.

According to such an amplification optical fiber with an optical component, pumping light output from the amplification optical fiber can be efficiently input again to the amplification optical fiber.

Preferably, in the amplification optical fiber with an optical component described above, at least a pair out of the optical fibers has optical path lengths different from each other.

If pumping lights on the same phase simultaneously output from the amplification optical fiber are input again on the same phase to the amplification optical fiber via the optical fiber, the intensity of the pumping lights input again may be lowered due to mode interference. However, with such an optical component, pumping lights on the same phase input to the respective optical fibers having different optical path lengths from one another are prevented from being output on the same phase. Therefore, mode interference is prevented from being caused among pumping lights that are output from the respective optical fibers having different optical path lengths from one another and input again to the amplification optical fiber.

Preferably, in the amplification optical fiber with an optical component described above, the optical component further includes a capillary having a plurality of through-holes, and the first end and the second end of the optical fiber are inserted into and passed through the through-holes, respectively.

According to such an amplification optical fiber with an optical component, the first end and the second end of the optical fiber can be easily coupled to the clad of the amplification optical fiber by adjusting the positions of the through-holes in the capillary and adjusting the position of the capillary.

Preferably, in the amplification optical fiber with an optical component described above, the optical fiber and the capillary are integrated with each other.

According to such an amplification optical fiber with an optical component, misalignment between the capillary and the optical fiber can be prevented.

Preferably, in the amplification optical fiber with an optical component described above, the optical component is arranged between the amplification optical fiber and the optical fiber, and further includes a bridge fiber having a bridge core coupled to the core of the amplification optical fiber and a bridge clad coupled to the clad of the amplification optical fiber and to the first end and the second end of the optical fiber, and the bridge clad has an outer diameter equal to or larger than that of the clad of the amplification optical fiber at an end on the amplification optical fiber side, and an outer diameter larger than that at the end on the amplification optical fiber side at an end on the optical fiber side.

According to such an amplification optical fiber with an optical component, since the clad of the bridge fiber has a larger diameter on the side of the optical fiber than on the side of the amplification optical fiber, the position of the optical fiber can be easily adjusted for coupling the optical fiber to the amplification optical fiber.

Preferably, in the amplification optical fiber with an optical component described above, the optical component further includes a second optical fiber coupled to the core of the amplification optical fiber at the first end thereof.

According to such an amplification optical fiber with an optical component, light output from the core of the amplification optical fiber can be easily output through the second optical fiber of the optical component.

Preferably, in the amplification optical fiber with an optical component described above, the optical component further includes a capillary having a plurality of through-holes, and the first end and the second end of the optical fiber as well as the second optical fiber are inserted into and passed through the through-holes, respectively.

According to such an amplification optical fiber with an optical component, the first end and the second end of the optical fiber can be easily coupled to the clad of the amplification optical fiber and the second optical fiber can be easily coupled to the core of the amplification optical fiber by adjusting the positions of the through-holes in the capillary and adjusting the position of the capillary.

Preferably, in the amplification optical fiber with an optical component described above, the optical fiber and the second optical fiber are integrated with the capillary.

According to such an amplification optical fiber with an optical component, misalignment between the capillary and the optical fiber and between the capillary and the second optical fiber can be prevented.

Preferably, in the amplification optical fiber with an optical component described above, the optical component is arranged between the amplification optical fiber and the optical fiber, and further includes a bridge fiber having a bridge core coupled to the core of the amplification optical fiber and to the second optical fiber and a bridge clad coupled to the clad of the amplification optical fiber and to the first end and the second end of the optical fiber, and the bridge clad has an outer diameter equal to or larger than that of the clad of the amplification optical fiber at an end on the amplification optical fiber side, and an outer diameter larger than that at the end on the amplification optical fiber side at an end on the optical fiber side.

According to such an amplification optical fiber with an optical component, since the clad of the bridge fiber has a larger diameter on the side of the optical fiber than on the side of the amplification optical fiber, the positions of the optical fiber and the second optical fiber can be easily adjusted for coupling the optical fiber and the second optical fiber to the amplification optical fiber.

A fiber laser device according to the invention includes: any one of the amplification optical fibers with an optical component described above; a seed light source configured to output seed light propagating through the core of the amplification optical fiber; and a pumping light source configured to output pumping light propagating through the clad of the amplification optical fiber, wherein the pumping light output from the pumping light source propagates through the clad along a direction from a second end toward the first end of the amplification optical fiber.

According to such a fiber laser device, even if pumping light propagating through the clad is output through the first end of the amplification optical fiber, at least part of the output pumping light can be input again to the amplification optical fiber by means of the optical fiber of the optical component coupled to the amplification optical fiber. Therefore, pumping light can be efficiently absorbed in the amplification optical fiber. Therefore, seed light can be efficiently amplified.

Alternatively, a fiber laser device according to the invention includes: any one of the amplification optical fibers with an optical component described above; a pumping light source configured to output pumping light propagating through the clad of the amplification optical fiber; and a pair of mirrors each coupled to the core of the amplification optical fiber at each end of the amplification optical fiber and configured to reflect at least light having a predetermined wavelength of spontaneous emission light emitted by the active element at reflectances different from each other, wherein the pumping light output from the pumping light source propagates through the clad along a direction from a second end toward the first end of the amplification optical fiber.

According to such a fiber laser device, even if pumping light propagating through the clad is output through the first end of the amplification optical fiber, at least part of the output pumping light can be input again to the amplification optical fiber by means of the optical fiber of the optical component coupled to the amplification optical fiber. Therefore, pumping light can be efficiently absorbed in the amplification optical fiber. Therefore, resonant light can be efficiently amplified between a pair of mirrors.

As described above, an amplification optical fiber with an optical component capable of efficiently absorbing pumping light and a fiber laser device including the same are provided according to the invention.

BEST MODE FOR CARRYING OUT THE INVENTION

Figure 1:
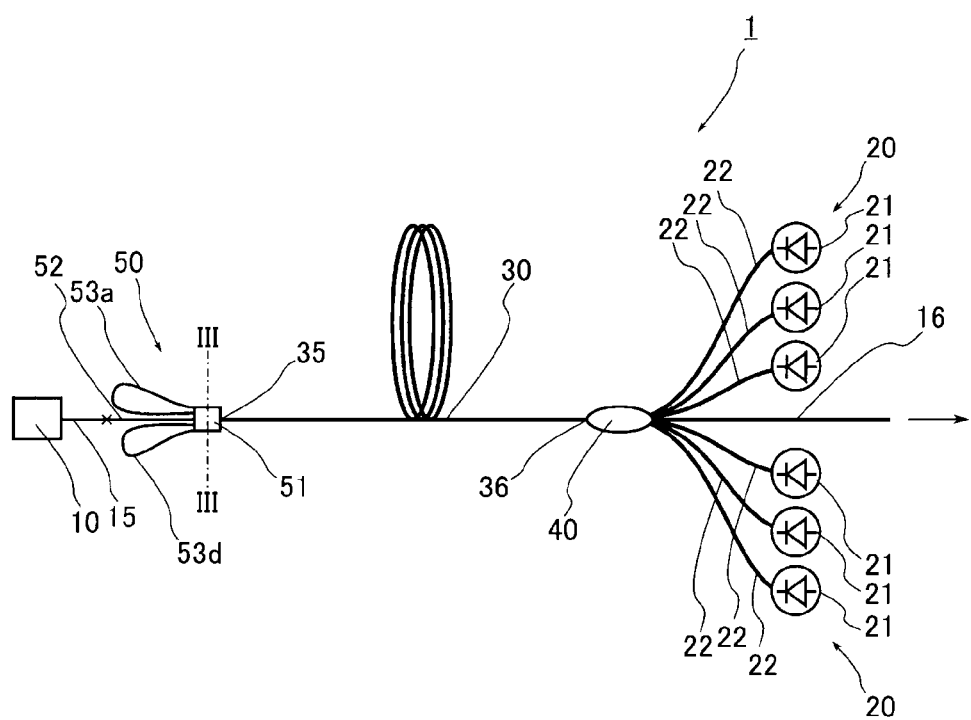
FIG. 1 is a schematic diagram showing a fiber laser device according to a first embodiment of the invention.

Preferred embodiments of an amplification optical fiber with an optical component and a fiber laser device including the same according to the invention will be described hereinafter referring to the drawings.
(First Embodiment)

FIG. 1 is a schematic diagram showing a fiber laser device according to a first embodiment of the invention.

As shown in FIG. 1, a fiber laser device 1 includes, as main components: a seed light source 10 configured to output seed light; a pumping light source 20 configured to output pumping light; an amplification optical fiber 30 to which the seed light and the pumping light are input; an optical component 50 coupled to the amplification optical fiber at a first end 35 of the amplification optical fiber 30; an output fiber 16 to which light output from the amplification optical fiber 30 is input; and a combiner 40 configured to couple the output fiber 16 and the pumping light source 20 to the amplification optical fiber 30 at a second end 36 of the amplification optical fiber 30. The optical component 50 and the amplification optical fiber 30 constitute an amplification optical fiber with an optical component.

The seed light source 10 may be constituted by a laser light source including a laser diode or by a fiber laser device of fabry-perot type or fibering type, for example. The seed light output from the seed light source 10 may be laser light having a wavelength of 1070 nm, for example, but is not particularly limited thereto. The seed light source 10 is connected to a fiber 15 for propagation of seed light having a core and a clad coating the core. The seed light output from the seed light source 10 propagates through the core of the fiber 15 for propagation of seed light. The fiber 15 for propagation of seed light may be a single mode fiber, for example, in which case the seed light propagates as single mode light through the fiber 15 for propagation of seed light.

The pumping light source 20 is constituted by a plurality of laser diodes 21, and configured to output pumping light having a wavelength of 915 nm, for example, when the seed light has a wavelength of 1070 nm as described above. The laser diodes 21 of the pumping light source 20 are connected to fibers 22 for propagation of pumping light, respectively. Pumping light output from each laser diode 21 propagates through the corresponding fiber 22 for propagation of pumping light. The fiber 22 for propagation of pumping light may be a multi mode fiber, for example, in which case the pumping light propagates as multi mode light through the fiber 22 for propagation of pumping light.

Figure 2:
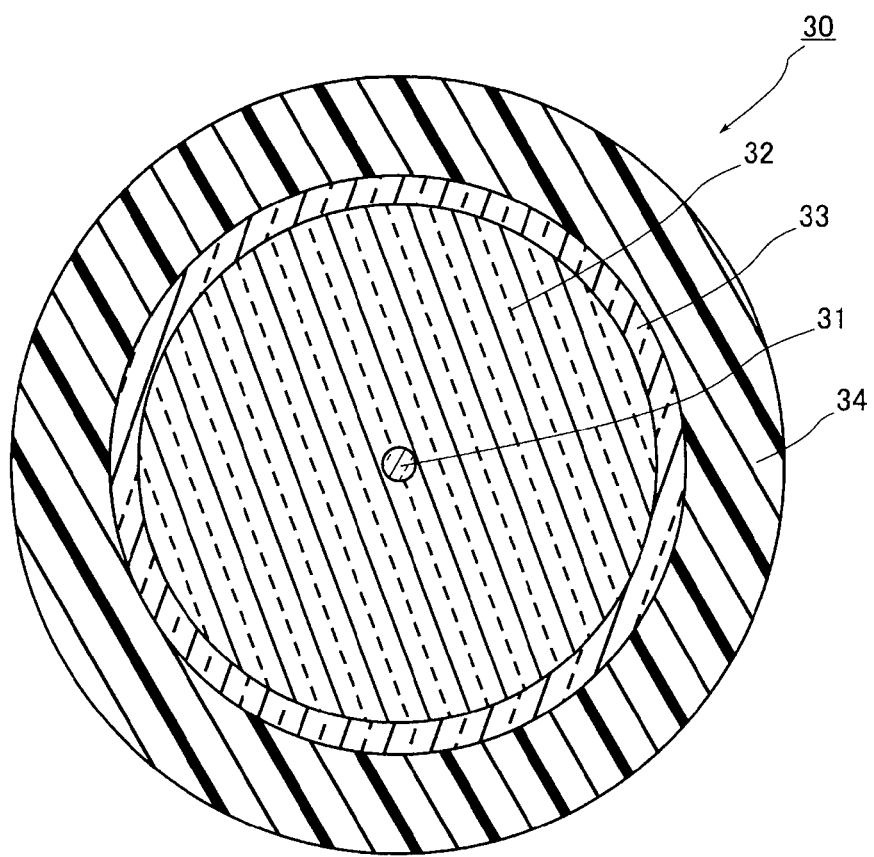
FIG. 2 is a view showing a structure of a cross-section perpendicular to a longitudinal direction of an amplification optical fiber shown in FIG. 1.

FIG. 2 is a view showing the structure of a cross-section perpendicular to the longitudinal direction of the amplification optical fiber 30. As shown in FIG. 2, the amplification optical fiber 30 has a core 31, a clad 32 coating the core 31, a plastic clad 33 coating the clad 32, and a coating layer 34 coating the plastic clad 33. The clad 32 has a lower refractive index than the core 31, and the plastic clad 33 has a further lower refractive index than the clad 32. A material for the core 31 may be silica doped with an element such as germanium (Ge) that increases the refractive index and an active element such as ytterbium (Yb) that is pumped by pumping light output from the pumping light source 20, for example. Such an active element may be a rare earth element, examples of which include thulium (Tm), cerium (Ce), neodymium (Nd), europium (Eu) and erbium (Er) in addition to Yb. Examples of the active element also include bismuth (Bi) or the like in addition to the rare earth element. A material for the clad 32 may be pure silica without any dopant, for example. A material for the plastic clad 33 may be UV curable resin, for example, and a material for the coating layer 34 may be UV curable resin different from that for the plastic clad 33, for example.

The output fiber 16 has a core and a clad coating the core, and is constituted by a single mode fiber similar to that for the fiber 15 for propagation of seed light, for example. A first end of the output fiber 16 is an output end.

The combiner 40 connects the output fiber 16 and the respective fibers 22 for propagation of pumping light with the amplification optical fiber 30 at the second end 36 of the amplification optical fiber 30. Specifically, the core of the output fiber 16 is connected end-to-end to the core 31 of the amplification optical fiber 30 in the combiner 40. Further, cores of the respective fibers 22 for propagation of pumping light are connected end-to-end to the clad 32 in the combiner 40. Accordingly, pumping light output from the pumping light source 20 is input to the clad 32 through the second end 36 of the amplification optical fiber 30, and light output through the second end 36 of the amplification optical fiber 30 is input to the output fiber 16. The fiber laser device 1 thus has a so-called backward-pumped configuration in which pumping light is input through an output end of the amplification optical fiber 30.

Figure 3:
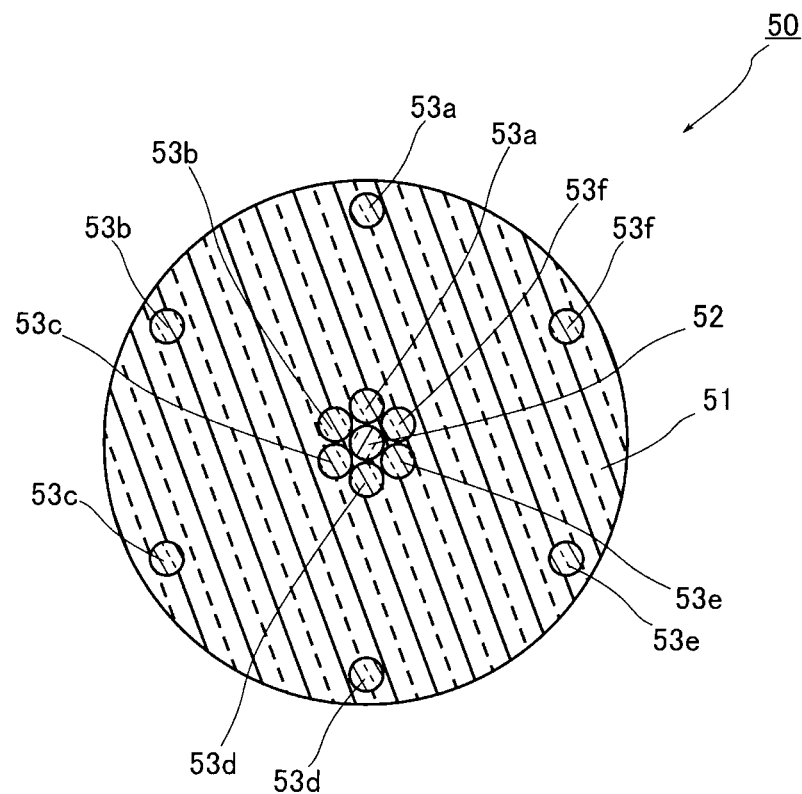
FIG. 3 is a view showing a structure of a cross-section of an optical component taken along a line III-III of FIG. 1.
Figure 4:
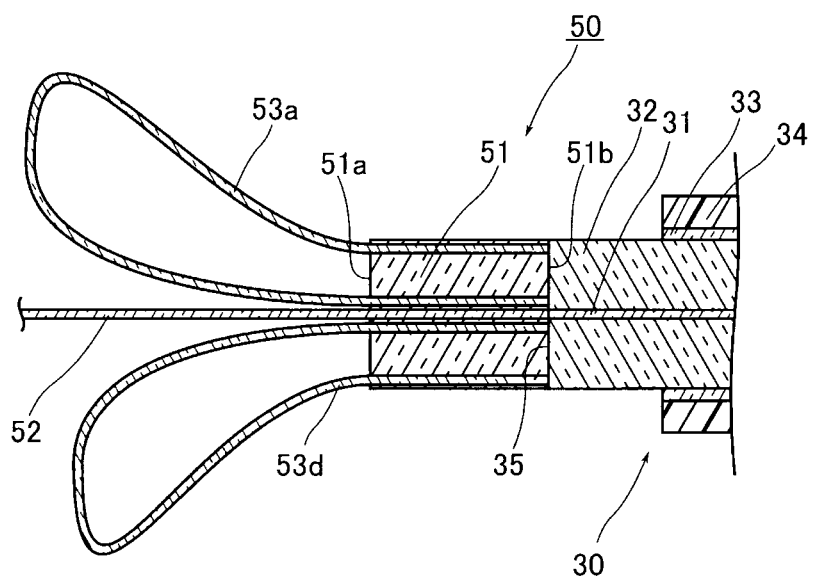
FIG. 4 is a view showing a structure of a cross-section along a longitudinal direction of the optical component shown in FIG. 1.

FIG. 3 is a view showing the structure of a cross-section of the optical component 50 taken along a line III-III of FIG. 1, and FIG. 4 is a view showing the structure of a cross-section along the longitudinal direction of the optical component. As shown in FIGS. 3 and 4, the optical component 50 includes: a capillary 51 having a plurality of through-holes; a plurality of optical fibers 53a to 53f, both ends of which are inserted in the through-holes of the capillary 51; and a second optical fiber 52 having one end inserted in a through-hole of the capillary 51.

As shown in FIGS. 3 and 4, the capillary 51 has a cylindrical shape with a diameter substantially equal to the outer diameter of the clad 32 of the amplification optical fiber 30, and has a plurality of through-holes extending from a first end 51a to a second end 51b.

The second optical fiber 52 has a core and a clad. In this embodiment, the core and the clad of the second optical fiber are made of silicas different in refractive index from each other. The one end of the second optical fiber 52 is inserted in and passed through a through-hole formed at the center in the diametrical direction of the capillary 51, and is flush with the second end 51b of the capillary 51. In FIGS. 3 and 4, the clad of the second optical fiber 52 is not illustrated.

The optical fibers 53a to 53f each have a core and a clad. In this embodiment, the core and the clad of each of the optical fibers 53a to 53f are made of silicas different in refractive index from each other. The difference in refractive index between the core and the clad of each of the optical fibers 53a to 53f is set so that light having a wavelength equal to that of pumping light output from the pumping light source 20 can be confined in the core and further that light having a wavelength equal to that of pumping light output from the pumping light source 20 can be confined in the core even if the optical fibers 53a to 53f are curved in loops as will be described later. In this embodiment, the optical fibers 53a to 53f have optical properties equal to one another and lengths different from one another. The optical fibers 53a to 53f thus have optical path lengths different from one another.

First ends of the optical fibers 53a to 53f are inserted in and passed through respective through-holes formed in the outer periphery of the capillary 51, and are flush with the second end 51b of the capillary 51. Second ends of the optical fibers 53a to 53f are inserted in and passed through respective through-holes formed in the inner periphery of the capillary 51 to be adjacent to the second optical fiber, and the second ends of the optical fibers 53a to 53f are flush with the second end 51b of the capillary 51. Accordingly, the optical fibers 53a to 53f are curved in loops at middle portions thereof, both ends of the optical fibers 53a to 53f face in the same direction, and the respective ends are inserted into the through-holes formed in the capillary 51 from the first end 51a side. In FIGS. 3 and 4, the clads of the respective optical fibers 53a to 53f are not illustrated.

The second optical fiber 52, the one end of which is inserted into a through-hole of the capillary 51 as described above, and the optical fibers 53a to 53f, both ends of which are inserted into through-holes of the capillary 51 as described above, are integrated with the capillary 51. The second optical fiber 52 and the optical fibers 53a to 53f can be integrated with the capillary 51 by heating the capillary 51 in a state where the first ends and the second ends of the respective optical fibers 53a to 53f are inserted into the plurality of through-holes. The heating can be carried out by using a $CO_2$ laser, an oxyhydrogen flame, or electric-discharge machining.

The optical component 50 is connected to the first end 35 of the amplification optical fiber 30. Specifically, the first end 35 of the amplification optical fiber 30 is connected to the second end 51b of the capillary 51 of the optical component 50 so that the core 31 of the amplification optical fiber 30 is connected to the core of the second optical fiber 52. Thus, the first ends of the respective optical fibers 53a to 53f are connected to a portion of the clad 32 in the outer periphery of the clad and the second ends thereof are connected to another portion of the clad 32 in the inner periphery of the clad 32 at the first end 35 of the amplification optical fiber 30.

Preferably, the core of the second optical fiber 52 has a refractive index equal to that of the core 31 of the amplification optical fiber 30, and the cores of the respective optical fibers 53a to 53f have a refractive index equal to that of the clad of the amplification optical fiber 30. In this case, a material for the core of the second optical fiber 52 may be silica doped with an element such as germanium that increases the refractive index, for example, similarly to the material for the core 31 of the amplification optical fiber 30. In addition, a material for the cores of the respective optical fibers 53a to 53f may be pure silica without any dopant similarly to the material for the clad 32 of the amplification optical fiber 30.

As shown in FIG. 1, the fiber 15 for propagation of seed light and the second optical fiber 52 are connected to each other, and the core of the fiber 15 for propagation of seed light and the core of the second optical fiber 52 are coupled to each other.

Next, an operation of the fiber laser device 1 will be described.

First, seed light that is light to be amplified is output from the seed light source 10 and pumping light is output from the pumping light source 20. The seed light output from the seed light source 10 has a wavelength of 1070 nm, for example, as described above. The seed light output from the seed light source 10 propagates through the core of the fiber 15 for propagation of seed light, is then input to the second optical fiber 52 of the optical component 50, and propagates through the second optical fiber 52. The seed light is then output from the second optical fiber 52, enters the core 31 through the first end 35 of the amplification optical fiber 30, and propagates through the core 31.

Pumping light output from each laser diode 21 of the pumping light source 20 has a wavelength of 915 nm, for example, as described above. The pumping light output from each laser diode 21 propagates through the fiber 22 for propagation of pumping light, enters the combiner 40, then enters the clad 32 through the second end 36 of the amplification optical fiber 30, and propagates mainly through the clad 32 along a direction from the second end 36 toward the first end 35 of the amplification optical fiber 30.

In the amplification optical fiber 30, the pumping light is absorbed by the active element doped in the core 31 and pumps the active element while passing through the core 31. The pumped active element causes stimulated emission, and the seed light is amplified by the stimulated emission, output through the second end 36 of the amplification optical fiber 30 as output light, and input to the output fiber 16. The seed light is then output through the output end of the output fiber 16.

The light output from the core 31 of the amplification optical fiber 30 enters the output fiber 16 and is output through the output end of the output fiber.

In the amplification optical fiber 30, part of pumping light in skew mode or the like that is not absorbed by the active element propagates mainly through the clad 32 and is output through the first end 35 of the amplification optical fiber 30. The output part of pumping light is then input to the respective optical fibers 53a to 53f. Specifically, pumping light output from the outer periphery of the clad 32 through the first end 35 of the amplification optical fiber 30 is input to the first ends of the respective optical fibers 53a to 53f inserted in the through-holes in the outer periphery of the capillary 51. Similarly, pumping light output from the inner periphery of the clad 32 through the first end 35 of the amplification optical fiber 30 is input to the second ends of the respective optical fibers 53a to 53f inserted in the through-holes in the inner periphery of the capillary 51. The pumping light input to the first ends of the respective optical fibers 53a to 53f is output through the second ends of the respective optical fibers 53a to 53f, and the pumping light input to the second ends of the respective optical fibers 53a to 53f is output through the first ends of the respective optical fibers 53a to 53f. The pumping lights thus output from the first ends and the second ends of the optical fibers 53a to 53f are input to the clad 32 of the amplification optical fiber 30 and absorbed by the active element while propagating mainly through the clad 32.

As described above, the optical fibers 53a to 53f have optical path lengths different from one another. As a result, the pumping lights output from the amplification optical fiber 30 on the same phase are prevented from being output from the respective optical fibers 53a to 53f as lights on the same phase. Therefore, mode interference is prevented from being caused among pumping lights that are output from the respective optical fibers and input again to the amplification optical fiber 30.

As described above, according to the amplification optical fiber with an optical component of this embodiment, pumping light output from the outer periphery that is a portion of the clad 32 is input to the respective optical fibers 53a to 53f of the optical component 50 through the first ends of the optical fibers 53a to 53f even when the pumping light is input to the second end 36 of the amplification optical fiber 30 and output from the clad 32 through the first end 35 of the amplification optical fiber 30. The pumping lights then propagate through the optical fibers 53a to 53f, are output through the second ends of the respective optical fibers 53a to 53f, and are input again to the clad 32 of the amplification optical fiber 30. On the other hand, pumping lights output from the inner periphery that is another portion of the clad 32 of the amplification optical fiber 30 are input to the respective optical fibers 53a to 53f through the second ends of the optical fibers 53a to 53f. The pumping lights then propagate through the optical fibers 53a to 53f, are output through the first ends of the respective optical fibers 53a to 53f, and are input again to the clad 32 of the amplification optical fiber 30. The pumping lights thus input again to the clad 32 of the amplification optical fiber 30 are absorbed by the active element while passing through the core 31. In this manner, according to the amplification optical fiber with an optical component of this embodiment, pumping light output from the amplification optical fiber 30 can be input again to the amplification optical fiber 30. Therefore, pumping light can be efficiently absorbed in the amplification optical fiber 30. Therefore, the fiber laser device 1 of this embodiment can efficiently amplify the seed light.

Moreover, the optical component 50 can input pumping light output from the outer periphery of the clad 32 to the inner periphery of the clad 32. It is to be noted here that skew mode light of pumping light propagating through the clad 32 of the amplification optical fiber 30 propagates mainly through the outer periphery of the clad 32. Therefore, according to the amplification optical fiber with an optical component, inputting the skew mode light output from the outer periphery of the clad 32 to the inner periphery of the clad 32 allows easy passage of the light through the core 31 in the amplification optical fiber 30. Therefore, pumping light can be more efficiently absorbed in the amplification optical fiber 30.

Since the second optical fiber 52 and both ends of the respective optical fibers 53a to 53f of the optical component 50 are inserted into the through-holes of the capillary 51, the first ends and the second ends of the respective optical fibers 53a to 53f can be easily coupled to the clad 32 of the amplification optical fiber 30 by adjusting the positions of the through-holes in the capillary 51 in advance and adjusting the position of the capillary 51.

When the core of the second optical fiber 52 has a refractive index equal to that of the core 31 of the amplification optical fiber 30, light output from the core of the amplification optical fiber 30 is more easily input to the second optical fiber 52. Moreover, when the cores of the respective optical fibers 53a to 53f have a refractive index equal to that of the clad of the amplification optical fiber 30, light output from the clad of the amplification optical fiber 30 is more easily input to the respective optical fibers 53a to 53f, and pumping lights output from the respective optical fibers 53a to 53f are more easily input to the clad 32.

(Second Embodiment)

Figure 5:
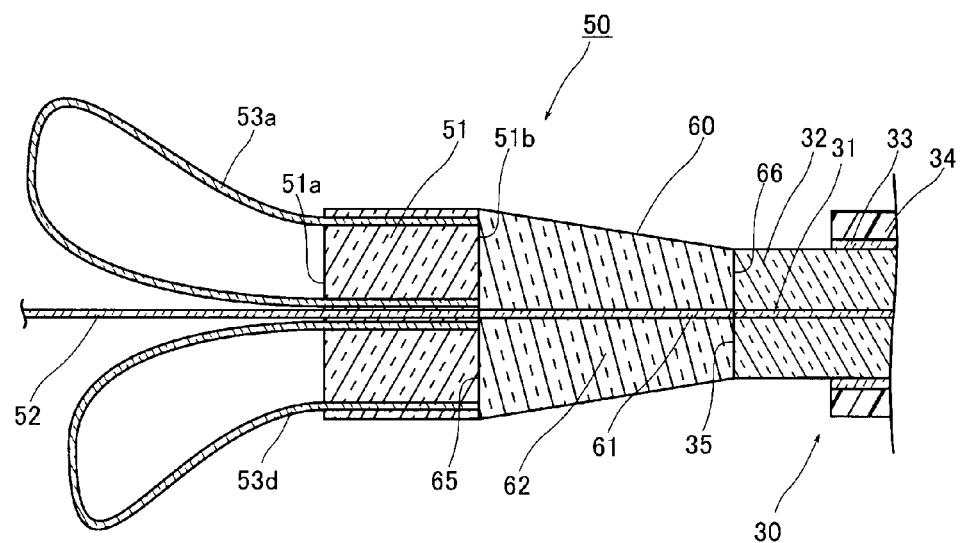
FIG. 5 is a view showing a structure of a cross-section along a longitudinal direction of an optical component of a fiber laser device according to a second embodiment of the invention.

Next, a second embodiment of the invention will be described in detail referring to FIG. 5. Here, components that are identical or similar to those in the first embodiment are indicated by the same reference numerals and the same description will not be repeated unless otherwise particularly described. FIG. 5 is a view showing the structure of a cross-section along the longitudinal direction of an optical component of a fiber laser device according to the second embodiment of the invention.

As shown in FIG. 5, the fiber laser device of this embodiment is different from the fiber laser device 1 of the first embodiment in that the optical component 50 includes a bridge fiber 60, and that the diameter of the capillary 51 is larger than the outer diameter of the clad 32 of the amplification optical fiber 30.

The bridge fiber 60 has a bridge core 61 and a bridge clad 62. The bridge fiber 60 is arranged between the capillary 51 and the amplification optical fiber 30, and the bridge clad 62 thereof has an outer diameter equal to the diameter of the capillary 51 at a first end 65 on the side of the optical fibers 53a to 53f. In addition, the bridge clad 62 of the bridge fiber 60 has an outer diameter equal to that of the clad 32 of the amplification optical fiber 30 at a second end 66 on the side of the amplification optical fiber 30. Therefore, the outer diameter of the bridge fiber 60 is larger at the first end 65 on the side of the optical fibers 53a to 53f than at the second end 66. The outer circumferential face of the bridge clad 62 is inclined with respect to a direction along the longitudinal direction. The bridge clad 62 of the bridge fiber 60 at the second end 66 may have an outer diameter larger than that of the clad 32 of the amplification optical fiber 30 only if the bridge clad 62 at the first end 65 has an outer diameter larger than that at the second end 66.

The first end 65 of the bridge fiber 60 is connected end-to-end to the second end 51b of the capillary 51, and the second end 66 of the bridge fiber 60 is connected end-to-end to the first end 35 of the amplification optical fiber 30. The bridge core 61 is thus coupled to the core of the amplification optical fiber 30 and the second optical fiber 52, and the bridge clad 62 is coupled to the clad 32 of the amplification optical fiber 30 and the first ends and the second ends of the respective optical fibers 53a to 53f. As described above, the optical component 50 including the bridge fiber 60 is connected to the amplification optical fiber 30 to form the amplification optical fiber with an optical component in this embodiment.

According to the amplification optical fiber with an optical component of this embodiment, the bridge clad 62 on the side of the optical fibers 53a to 53f has an outer diameter larger than that on the side of the amplification optical fiber 30. Accordingly, the positions of the respective optical fibers 53a to 53f and the second optical fiber 52 can be easily adjusted in coupling the optical fibers 53a to 53f and the second optical fiber 52 to the amplification optical fiber 30. Therefore, the fiber laser device 1 of this embodiment can be easily assembled.

(Third Embodiment)

Figure 6:
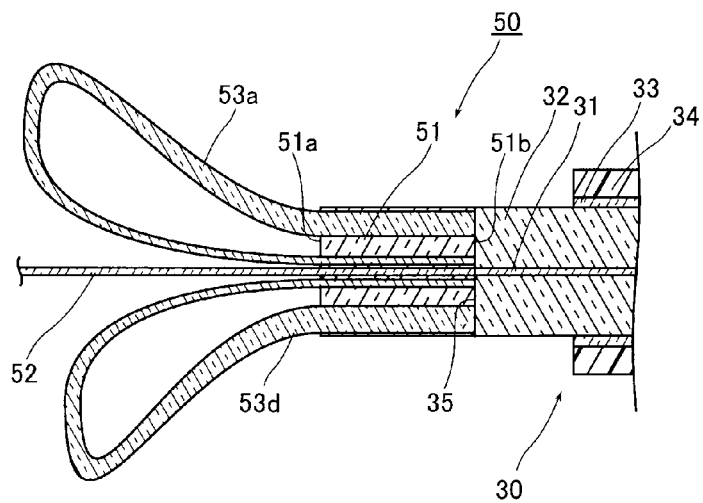
FIG. 6 is a view showing a structure of a cross-section along a longitudinal direction of an optical component of a fiber laser device according to a third embodiment of the invention.

Next, a third embodiment of the invention will be described in detail referring to FIG. 6. Here, components that are identical or similar to those in the first embodiment are indicated by the same reference numerals and the same description will not be repeated unless otherwise particularly described. FIG. 6 is a view showing a structure of a cross-section along the longitudinal direction of an optical component of a fiber laser device according to the third embodiment of the invention.

As shown in FIG. 6, the fiber laser device of this embodiment is different from the fiber laser device 1 of the first embodiment in that the cross-sectional areas of the respective optical fibers 53a to 53f of the optical component 50 at the first ends are larger than those at the second ends. Specifically, in the amplification optical fiber with an optical component, the optical fibers 53a to 53f are coupled to the clad 32 of the amplification optical fiber 30 at large areas in the outer periphery of the clad 32, and the optical fibers 53a to 53f are coupled to the clad 32 of the amplification optical fiber 30 at small areas in the inner periphery of the clad 32.

According to the amplification optical fiber with an optical component of this embodiment, larger part of pumping light output from the outer periphery of the clad 32 of the amplification optical fiber 30 can be input to the inner periphery of the amplification optical fiber 30. As described above, skew mode light of pumping light propagating through the clad 32 of the amplification optical fiber 30 propagates mainly through the outer periphery of the clad 32. Thus, according to the optical component 50 of this embodiment, larger part of skew mode light can be input to the inner periphery of the clad 32 through the respective optical fibers 53a to 53f.

(Fourth Embodiment)

Figure 7:
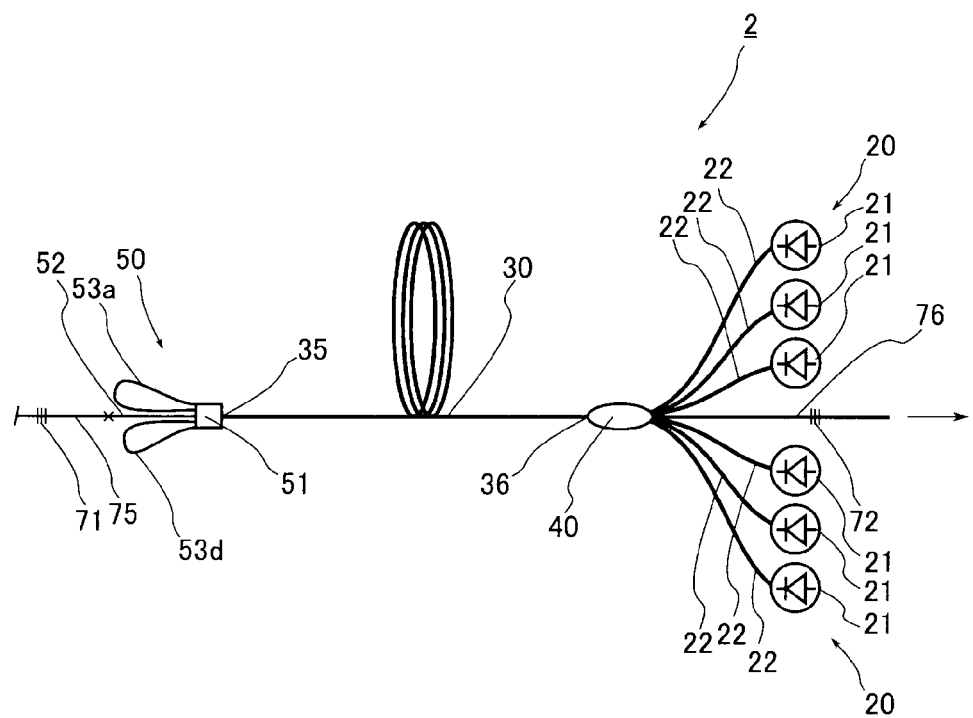
FIG. 7 is a schematic diagram showing a fiber laser device according to a fourth embodiment of the invention.

Next, a fourth embodiment of the invention will be described in detail referring to FIG. 7. Here, components that are identical or similar to those in the first embodiment are indicated by the same reference numerals and the same description will not be repeated unless otherwise particularly described. FIG. 7 is a schematic diagram showing a fiber laser device according to a fourth embodiment of the invention.

As shown in FIG. 7, a fiber laser device 2 of this embodiment includes, as main components: a pumping light source 20 configured to output pumping light; an amplification optical fiber 30 to which the pumping light is input; an optical component 50 coupled to the amplification optical fiber 30 at a first end 35 of the amplification optical fiber 30; a first resonance fiber 75 coupled to the first end 35 of the amplification optical fiber 30 through the optical component 50; a second resonance fiber 76 coupled to a second end 36 of the amplification optical fiber 30; a first fiber bragg grating (FBG) 71 that is a first mirror provided to the first resonance fiber 75; a second FBG 72 that is a second mirror provided to the second resonance fiber 76; and a combiner 40 configured to couple the second resonance fiber 76 and the pumping light source 20 to the amplification optical fiber 30 at the second end 36 of the amplification optical fiber 30. The optical component 50 and the amplification optical fiber 30 constitute an amplification optical fiber with an optical component.

The first resonance fiber 75 has a core and a clad, and has the same structure as that of the fiber 15 for propagation of seed light in the first embodiment, for example. The first resonance fiber 75 and the second optical fiber 52 are connected to each other in a manner that the core of the first resonance fiber 75 and the core of the second optical fiber 52 are coupled to each other. Therefore, the core of the first resonance fiber 75 is coupled to the core 31 of the amplification optical fiber 30 through the core of the second optical fiber 52. The first FBG 71 is arranged in the core of the first resonance fiber 75, and coupled to the core 31 of the amplification optical fiber 30. The first FBG 71 is configured to reflect light having a wavelength equal to that of part of spontaneous emission light emitted when the active element doped in the core 31 of the amplification optical fiber 30 is pumped at a reflectance of 100%, for example.

The second resonance fiber 76 has a core and a clad, and has the same structure as that of the output fiber 16 in the first embodiment, for example. The second resonance fiber 76 is connected to the amplification optical fiber 30 at the combiner 40 where the core 31 of the amplification optical fiber 30 is coupled to the core of the second resonance fiber 76 in a manner similar to the connection between the amplification optical fiber 30 and the output fiber 16 in the first embodiment. The second FBG 72 is arranged in the core of the second resonance fiber 76, and coupled to the core 31 of the amplification optical fiber 30. The second FBG 72 is configured to reflect light having a wavelength equal to that reflected by the first FBG 71 at a lower reflectance than the first FBG 71. The reflectance of the second FBG is 30%, for example. An end of the second resonance fiber 76 on a side opposite to the combiner is an output end. The fiber laser device 2 thus has a so-called backward-pumped configuration in which pumping light is input through an output end of the amplification optical fiber.

In such a fiber laser device 2, pumping light is first output from each of the laser diodes 21 of the pumping light source 20. Pumping light output from each laser diode 21 has a wavelength of 915 nm, for example, as described above. The pumping light output from each laser diode 21 propagates through the fiber 22 for propagation of pumping light, enters the combiner 40, then enters the clad 32 through the second end 36 of the amplification optical fiber 30, and propagates mainly through the clad 32. The pumping light is absorbed by the active element doped in the core 31 and pumps the active element while passing through the core 31.

The active element thus pumped by the pumping light emits spontaneous emission light, which causes resonance between the first FBG 71 and the second FBG 72. Resonant light has a wavelength equal to that of reflected light from the first FBG 71 and the second FGB 72. The resonant light that is light to be amplified is amplified by the stimulated emission caused by the active element in the amplification optical fiber 30. Part of the amplified light passes through the second FBG 72 and is output as output light.

In this case, part of the pumping light output through the first end 35 of the amplification optical fiber without being absorbed by the active element in the amplification optical fiber 30 is input again to the clad 32 of the amplification optical fiber 30 via the respective optical fibers 53a to 53f of the optical component 50 and absorbed by the active element while propagating mainly through the clad 32 similarly to the fiber laser device 1 of the first embodiment.

According to the fiber laser device 2 of this embodiment, pumping light output from the amplification optical fiber 30 can be input again to the amplification optical fiber 30 with the amplification optical fiber with an optical component. Therefore, pumping light can be efficiently absorbed in the amplification optical fiber 30. Therefore, resonant light can be efficiently amplified in the amplification optical fiber 30.

Although the invention has been described above by reference to the first to fourth embodiments as examples, the invention is not limited thereto.

For example, the second optical fiber 52 is not necessarily needed as an optical component in the first to fourth embodiments. If the second optical fiber 52 is not used in the optical component 50, an optical fiber that can serve as a substitute for the second optical fiber 52 may be connected the core 31 of the amplification optical fiber 30.

In the first to fourth embodiments, the optical component 50 includes the capillary 51 having a plurality of through-holes formed therein and the respective optical fibers 53a to 53f and the second optical fiber 52 are integrated with the capillary 51. However, the respective optical fibers 53a to 53f and the second optical fiber 52 are not necessarily needed to be integrated with the capillary 51. Moreover, the capillary 51 is not necessarily needed as long as the respective optical fibers 53a to 53f and the second optical fiber 52 are coupled to the amplification optical fiber 30.

Although each of the optical fibers 53a to 53f of the optical component 50 is formed of one optical fiber in the first to fourth embodiments, each of the optical fibers 53a to 53f may be formed of a plurality of optical fibers connected to one another. However, optical fibers each formed of one optical fiber have no joint portions, and thus there is no loss of pumping light caused by joint portions. Therefore, pumping light output from the amplification optical fiber can be efficiently input again to the amplification optical fiber by using one optical fiber without any joint portion.

In the first to fourth embodiments, the respective optical fibers 53a to 53f of the optical component 50 have different lengths from one another. However, at least a pair out of the optical fibers 53a to 53f may be different from each other or all the optical fibers 53a to 53f may have equal length.

In the first to fourth embodiments, the optical component 50 includes a plurality of optical fibers 53a to 53f. However, the number of optical fibers may be either larger or smaller than that in the respective embodiments, or may be even one.

The second optical fiber 52 and the fiber 15 for propagation of seed light may be formed of one optical fiber in the first to third embodiments, and the second optical fiber 52 and the first resonance fiber 75 may be formed of one optical fiber in the fourth embodiment.

In the fiber laser device 1 according to the first to third embodiments, the second end 36 of the amplification optical fiber 30 is the output end, but the invention is not limited thereto. For example, the fiber 15 for propagation of seed light instead of the output fiber 16 may be connected to the amplification optical fiber 30 and the output fiber 16 may be connected to the second optical fiber 52 of the optical component 50 in the combiner 40 of the fiber laser device 1 of the first to third embodiments. With such a configuration, the fiber laser device 1 can have a so-called forward-pumped configuration in which pumping light is input through an input end of the seed light of the amplification optical fiber 30. In this case, the second optical fiber 52 and the output fiber 16 may be formed of one optical fiber.

Similarly, the first resonance fiber 75 instead of the second resonance fiber 76 may be connected to the amplification optical fiber 30 and the second resonance fiber may be connected to the second optical fiber 52 of the optical component 50 in the combiner 40 of the fiber laser device 2 of the fourth embodiment. Also in this case, the fiber laser device 2 can have a so-called forward-pumped configuration. In this case, the second optical fiber 52 and the second resonance fiber 76 may be formed of one optical fiber.

In the first to fourth embodiments, the cross-section of the clad 32 perpendicular to the longitudinal direction of the amplification optical fiber 30 may have a non-circular shape such as a polygonal shape or a D-shape.

In the first to fourth embodiments, the pumping light is input to the second end 36 of the amplification optical fiber 30 and propagates toward the first end 35. However, it may be configured such that the pumping light is input to a middle portion of the amplification optical fiber 30 and propagates through the clad 32 along a direction from the second end 36 toward the first end 35 of the amplification optical fiber 30.

EXAMPLES

The invention will be more specifically explained below with an example and a comparative example, but the invention is not limited thereto.

First Example

Six optical fibers having a core made of silica without any dopant with a diameter of 105 μm and a clad made of silica doped with fluorine (F) with an outer diameter of 125 μm were prepared. The optical fibers had lengths of 40 cm, 44 cm, 48 cm, 52 cm, 56 cm and 60 cm, respectively. In addition, a second optical fiber for signal light propagation having a core made of silica doped with Ge with a diameter of 10 μm and a clad made of silica without any dopant with an outer diameter of 125 μm was prepared. Further, a capillary made of silica having a cylindrical shape with an outer diameter of about 1000 μm and a length of 1 cm was prepared. The capillary had one through-hole with a diameter of 135 μm extending between the centers of both end surfaces thereof, six through-holes formed adjacent to the center through-hole with an equal diameter, and further six through-holes formed in the outer periphery with an equal diameter. First ends of the six optical fibers were passed through the through-holes in the outer periphery, and second ends of the six optical fibers were passed through the respective through-holes adjacent to the through-hole extending between the centers of both end surfaces. In addition, the second optical fiber was passed through the through-hole extending between the centers of both end surfaces. The capillary was heated by a $CO_2$ laser to integrate the first ends and the second ends of the six optical fibers as well as the second optical fiber with the capillary over a length of 8 mm. Then, the capillary, the six optical fibers and the second optical fiber were cut at the center in the longitudinal direction of the portion where the first ends and the second ends of the six optical fibers as well as the second optical fiber were integrated with the capillary so as to expose the end surfaces.

Next, a bridge fiber made of a double-clad fiber of 3 cm in length having a core with a diameter of 10 μm and a clad having a tapered outer circumferential face with an outer diameter of 500 μm at a first end thereof and an outer diameter of 1000 μm at a second end thereof was prepared. The core of the bridge fiber was made of silica doped with Ge, the clad thereof was made of silica without any dopant, and the clad was covered with a plastic clad.

Next, the second end of the bridge fiber was connected to an end surface of the capillary to couple the core of the bridge fiber to the core of the second optical fiber and the clad of the bridge fiber to the first ends and the second ends of the six optical fibers.

The optical component as shown in FIG. 5 was thus produced.

Next, an amplification optical fiber of 20 m in length having a core made of silica doped with Yb and Ge with a diameter of 10 μm, a clad made of silica without any dopant with an outer diameter of 500 μm, and a plastic clad covering the clad was prepared. Then, the bridge fiber of the optical component was connected to a first end of the amplification optical fiber to couple the core of the bridge fiber to the core of the amplification optical fiber and the clad of the bridge fiber to the clad of the amplification optical fiber. The amplification optical fiber with an optical component as shown in FIG. 5 was thus produced. Then, an optical fiber formed with a first FBG having a reflectance of 100% was connected to a second end of the amplification optical fiber, and a multi mode fiber for propagation of pumping light connected to a pumping light source was connected to the optical fiber. A configuration in which pumping light is input to the clad of the amplification optical fiber through the second end was thus obtained. Further, an optical fiber formed with a second FBG having a reflectance of 10% was connected to the second optical fiber of the optical component. A fiber laser device having a so-called forward pumped configuration in which pumping light is input to the amplification optical fiber through an end opposite to the output end thereof was thus produced.

First Comparative Example

A fiber laser device similar to that of the first example except for that the optical component was not provided and that the amplification optical fiber and the optical fiber formed with the second FBG were directly connected to each other was produced.

Next, 8 W of pumping light having a wavelength of 915 nm was made to be output from the pumping light source in each of the first example and the first comparative example. As a result of measuring the light amplification efficiency, it was 55% in the first example and 49% in the first comparative example.

Therefore, it can be concluded that pumping light was efficiently absorbed in the amplification optical fiber in the fiber laser device including the amplification optical fiber with an optical component of the first example.

Industrial Applicability

According to the invention, an amplification optical fiber with an optical component capable of efficiently absorbing pumping light and a fiber laser device including the same are provided.

DESCRIPTION OF REFERENCE NUMERALS 1, 2 . . . fiber laser device
10 . . . seed light source
15 . . . fiber for propagation of seed light
16 . . . output fiber
20 . . . pumping light source
21 . . . laser diode
22 . . . fiber for propagation of pumping light
30 . . . amplification optical fiber
31 . . . core
32 . . . clad
33 . . . plastic clad
34 . . . coating layer
40 . . . combiner
50 . . . optical component
51 . . . capillary
52 . . . second optical fiber
53a to 53f . . . optical fiber
60 . . . bridge fiber
61 . . . bridge core
62 . . . bridge clad
71 . . . first FBG
72 . . . second FBG
75 . . . first resonance fiber
76 . . . second resonance fiber

The invention claimed is:

1. An amplification optical fiber with an optical component, comprising:
   an amplification optical fiber having a core doped with an active element and a clad through which pumping light for amplifying light to be amplified propagating through the core propagates; and
   an optical component including at least one optical fiber having a first end coupled to a portion of the clad and a second end coupled to another portion of the clad at a first end of the amplification optical fiber such that the pumping light output from the clad is input to one of the first end of the at least one optical fiber and the second end of the at least one optical fiber, output through the other of the first end of the at least one optical fiber and the second end of the at least one optical fiber, and input to the clad.

2. The amplification optical fiber with an optical component according to claim 1, wherein the portion of the clad to which the first end of the optical fiber is coupled is nearer to an outer periphery of the amplification optical fiber than the another portion of the clad to which the second end of the optical fiber is coupled.

3. The amplification optical fiber with an optical component according to claim 2, wherein a cross-sectional area of the optical fiber at the first end is larger than that at the second end.

4. The amplification optical fiber with an optical component according to any one of claims 1 to 3, wherein the optical fiber is jointless.

5. The amplification optical fiber with an optical component according to any one of claims 1 to 3, wherein the optical component includes a plurality of optical fibers.

6. The amplification optical fiber with an optical component according to claim 5, wherein at least a pair out of the optical fibers has optical path lengths different from each other.

7. The amplification optical fiber with an optical component according to any one of claims 1 to 3, wherein the optical component further includes a capillary having a plurality of through-holes, and
   the first end and the second end of the optical fiber are inserted into and passed through the through-holes, respectively.

8. The amplification optical fiber with an optical component according to claim 7, wherein the optical fiber and the capillary are integrated with each other.

9. The amplification optical fiber with an optical component according to any one of claims 1 to 3, wherein the optical component is arranged between the amplification optical fiber and the optical fiber, and further includes a bridge fiber having a bridge core coupled to the core of the amplification optical fiber and a bridge clad coupled to the clad of the amplification optical fiber and to the first end and the second end of the optical fiber, and
   the bridge clad has an outer diameter equal to or larger than that of the clad of the amplification optical fiber at an end on the amplification optical fiber side, and an outer diameter larger than that at the end on the amplification optical fiber side at an end on the optical fiber side.

10. The amplification optical fiber with an optical component according to any one of claims 1 to 3, wherein the optical component further includes a second optical fiber coupled to the core of the amplification optical fiber at the first end thereof.

11. The amplification optical fiber with an optical component according to claim 10, wherein
the optical component further includes a capillary having a plurality of through-holes, and
the first end and the second end of the optical fiber as well as the second optical fiber are inserted into and passed through the through-holes, respectively.

12. The amplification optical fiber with an optical component according to claim 11, wherein the optical fiber and the second optical fiber are integrated with the capillary.

13. The amplification optical fiber with an optical component according to claim 10, wherein the optical component is arranged between the amplification optical fiber and the optical fiber, and further includes a bridge fiber having a bridge core coupled to the core of the amplification optical fiber and to the second optical fiber and a bridge clad coupled to the clad of the amplification optical fiber and to the first end and the second end of the optical fiber, and
the bridge clad has an outer diameter equal to or larger than that of the clad of the amplification optical fiber at an end on the amplification optical fiber side, and an outer diameter larger than that at the end on the amplification optical fiber side at an end on the optical fiber side.

14. A fiber laser device comprising:
the amplification optical fiber with an optical component according to any one of claims 1 to 3;
a seed light source configured to output seed light propagating through the core of the amplification optical fiber; and
a pumping light source configured to output pumping light propagating through the clad of the amplification optical fiber, wherein
the pumping light output from the pumping light source propagates through the clad along a direction from a second end toward the first end of the amplification optical fiber.

15. A fiber laser device comprising:
the amplification optical fiber with an optical component according to any one of claims 1 to 3;
a pumping light source configured to output pumping light propagating through the clad of the amplification optical fiber; and
a pair of mirrors each coupled to the core of the amplification optical fiber at respective ends of the amplification optical fiber and configured to reflect at least light having a predetermined wavelength of spontaneous emission light emitted by the active element at reflectances different from each other, wherein
the pumping light output from the pumping light source propagates through the clad along a direction from a second end toward the first end of the amplification optical fiber.

* * * * *